United States Patent
Karkanias et al.

(10) Patent No.: US 9,396,669 B2
(45) Date of Patent: Jul. 19, 2016

(54) SURGICAL PROCEDURE CAPTURE, MODELLING, AND EDITING INTERACTIVE PLAYBACK

(75) Inventors: Chris Demetrios Karkanias, Sammamish, WA (US); Michael J. Sinclair, Kirkland, WA (US); James R. Hamilton, Bellevue, WA (US); Oren Rosenbloom, Redmond, WA (US); Hubert Van Hoof, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 1815 days.

(21) Appl. No.: 12/139,960

(22) Filed: Jun. 16, 2008

(65) Prior Publication Data

US 2009/0311655 A1 Dec. 17, 2009

(51) Int. Cl.
G09B 23/28 (2006.01)
G06T 19/00 (2011.01)
(Continued)

(52) U.S. Cl.
CPC .............. *G09B 23/28* (2013.01); *A61B 1/0005* (2013.01); *A61B 1/00183* (2013.01);
(Continued)

(58) Field of Classification Search
CPC ........ G09B 23/28; G09B 23/285; G09B 5/14; G09B 23/30; G09B 23/32; G09B 23/34; G09B 5/00; G09B 5/065; G09B 9/00; A61B 1/005; A61B 1/00183; A61B 1/00193; A61B 1/018; A61B 1/04; A61B 1/042; A61B 1/3132; A61B 19/22; A61B 19/30; A61B 19/50; A61B 19/5212; A61B 19/5244; A61B 2017/00707; A61B 2017/00115; A61B 2017/00128; A61B 2017/3405; A61B 2019/223; A61B 2019/2211; A61B 2019/2223; A61B 2019/2292; A61B 2019/2296; A61B 2019/301; A61B 2019/464; A61B 2019/507; A61B 2019/5255; A61B 2019/5259; A61B 2019/5265; A61B 2019/5291; A61B 2019/5483; A61B 5/00; A61B 5/0215; A61B 5/061; A61B 5/1076; A61B 5/1455; B25J 9/1689; G06F 19/3418; G06F 19/3437; G06F 19/366; G06F 2203/015; G06F 3/016; G06T 15/00; G06T 19/00; G06T 2207/10021; G06T 2207/10068; G06T 2207/30004; G06T 2207/30241; G06T 2210/41

USPC .......................................................... 434/262

See application file for complete search history.

(56) References Cited

U.S. PATENT DOCUMENTS

| | | | | |
|---|---|---|---|---|
| 5,546,943 A | * | 8/1996 | Gould | 600/425 |
| 5,769,640 A | * | 6/1998 | Jacobus et al. | 434/262 |

(Continued)

FOREIGN PATENT DOCUMENTS

WO 9628800 A1 9/1996

OTHER PUBLICATIONS

Hai Vision Systems, Inc. Remote Medical Training, http://www.haivision.com/Downloads/App%20Note%20Remote%20Med%20Training.pdf. Last accessed Oct. 25, 2007. 1 page.

(Continued)

*Primary Examiner* — Nikolai A Gishnock
(74) *Attorney, Agent, or Firm* — Steve Wight; Sandy Swain; Micky Minhas

(57) ABSTRACT

A system for generating surgical procedure training media draws upon the realistic data of an actual surgical procedure for realistic training without the risks. A 3D capturing component records three-dimensional model plus imaging data over time of a portion of a patient's body undergoing a surgical procedure. A spatial detection system detects an orientation of a surgical instrument relative to the patient's body during the surgical procedure. A modeling component creates a four-dimensional model (3D model+time) of the portion of the patient's body. Animation such as contingent events, trainee prompts, a virtual surgical instrument, etc., can be added to the model to expand upon the training potential. A user interface processes and edits training media for playback of the four-dimensional model including defining triggers responsive to a trainee simulated surgical inputs to pace sequencing of playback. An interactive player responds to pacing the playback of the editing training media or to a spatially detected simulated surgical instrument held by the student for direct tissue interaction.

21 Claims, 7 Drawing Sheets

(51) Int. Cl.
| | |
|---|---|
| A61B 5/00 | (2006.01) |
| G06F 3/16 | (2006.01) |
| G09B 23/30 | (2006.01) |
| G09B 23/32 | (2006.01) |
| G09B 23/34 | (2006.01) |
| G09B 5/00 | (2006.01) |
| G09B 5/06 | (2006.01) |
| G09B 5/14 | (2006.01) |
| G09B 9/00 | (2006.01) |
| A61B 1/00 | (2006.01) |
| A61B 1/018 | (2006.01) |
| A61B 1/04 | (2006.01) |
| A61B 1/313 | (2006.01) |
| A61B 19/00 | (2006.01) |
| A61B 5/0215 | (2006.01) |
| A61B 5/06 | (2006.01) |
| A61B 5/107 | (2006.01) |
| A61B 5/1455 | (2006.01) |
| B25J 9/16 | (2006.01) |
| G06F 19/00 | (2011.01) |
| G06F 3/01 | (2006.01) |
| G06T 15/00 | (2011.01) |
| A61B 17/00 | (2006.01) |
| A61B 17/34 | (2006.01) |

(52) U.S. Cl.
CPC ............ *A61B 1/00193* (2013.01); *A61B 1/018* (2013.01); *A61B 1/04* (2013.01); *A61B 1/042* (2013.01); *A61B 1/3132* (2013.01); *A61B 5/00* (2013.01); *A61B 5/0215* (2013.01); *A61B 5/061* (2013.01); *A61B 5/1076* (2013.01); *A61B 5/1455* (2013.01); *A61B 19/22* (2013.01); *A61B 19/30* (2013.01); *A61B 19/50* (2013.01); *A61B 19/5212* (2013.01); *A61B 19/5244* (2013.01); *B25J 9/1689* (2013.01); *G06F 3/016* (2013.01); *G06F 19/3418* (2013.01); *G06F 19/3437* (2013.01); *G06F 19/366* (2013.01); *G06T 15/00* (2013.01); *G06T 19/00* (2013.01); *G09B 5/00* (2013.01); *G09B 5/065* (2013.01); *G09B 5/14* (2013.01); *G09B 9/00* (2013.01); *G09B 23/285* (2013.01); *G09B 23/30* (2013.01); *G09B 23/32* (2013.01); *G09B 23/34* (2013.01); *A61B 2017/00115* (2013.01); *A61B 2017/00128* (2013.01); *A61B 2017/00707* (2013.01); *A61B 2017/3405* (2013.01); *A61B 2019/223* (2013.01); *A61B 2019/2211* (2013.01); *A61B 2019/2223* (2013.01); *A61B 2019/2292* (2013.01); *A61B 2019/2296* (2013.01); *A61B 2019/301* (2013.01); *A61B 2019/464* (2013.01); *A61B 2019/507* (2013.01); *A61B 2019/5255* (2013.01); *A61B 2019/5259* (2013.01); *A61B 2019/5265* (2013.01); *A61B 2019/5291* (2013.01); *A61B 2019/5483* (2013.01); *G06F 2203/015* (2013.01); *G06T 2207/10021* (2013.01); *G06T 2207/10068* (2013.01); *G06T 2207/30004* (2013.01); *G06T 2207/30241* (2013.01); *G06T 2210/41* (2013.01)

(56) References Cited

U.S. PATENT DOCUMENTS

| | | | | |
|---|---|---|---|---|
| 5,769,641 | A | * | 6/1998 | Lampotang et al. .......... 434/272 |
| 5,791,907 | A | * | 8/1998 | Ramshaw et al. ............. 434/262 |
| 5,882,206 | A | * | 3/1999 | Gillio ............................ 434/262 |
| 6,077,082 | A | * | 6/2000 | Gibson et al. ................. 434/262 |
| 6,538,634 | B1 | * | 3/2003 | Chui et al. .................... 345/156 |
| 6,790,043 | B2 | | 9/2004 | Aboud |
| 6,863,536 | B1 | * | 3/2005 | Fisher et al. .................. 434/272 |
| 6,918,769 | B2 | * | 7/2005 | Rink ............................ 434/247 |
| 6,939,138 | B2 | * | 9/2005 | Chosack et al. .............. 434/262 |
| 7,121,832 | B2 | * | 10/2006 | Hsieh et al. ................... 434/262 |
| 7,239,992 | B2 | | 7/2007 | Ayache et al. |
| 7,485,115 | B2 | * | 2/2009 | Nakamura .................... 434/262 |
| 2002/0113863 | A1 | | 8/2002 | Levy |
| 2002/0149617 | A1 | | 10/2002 | Becker |
| 2004/0009459 | A1 | * | 1/2004 | Anderson et al. ............. 434/262 |
| 2004/0072134 | A1 | * | 4/2004 | Takahashi ..................... 434/262 |
| 2004/0175684 | A1 | * | 9/2004 | Kaasa et al. ................... 434/262 |
| 2004/0234933 | A1 | * | 11/2004 | Dawson et al. ............... 434/262 |
| 2005/0052527 | A1 | | 3/2005 | Remy et al. |
| 2005/0084833 | A1 | * | 4/2005 | Lacey et al. .................. 434/262 |
| 2005/0233290 | A1 | * | 10/2005 | Jackson ........................ 434/262 |
| 2005/0255434 | A1 | * | 11/2005 | Lok et al. ..................... 434/262 |
| 2006/0040245 | A1 | * | 2/2006 | Airola et al. .................. 434/262 |
| 2007/0005695 | A1 | | 1/2007 | Chen et al. |
| 2007/0118389 | A1 | | 5/2007 | Shipon |
| 2007/0172803 | A1 | * | 7/2007 | Hannaford et al. ........... 434/262 |
| 2007/0207448 | A1 | | 9/2007 | Glaser et al. |
| 2007/0218437 | A1 | | 9/2007 | Lotano et al. |
| 2007/0223574 | A1 | | 9/2007 | Roman et al. |
| 2008/0003555 | A1 | * | 1/2008 | Ekvall et al. .................. 434/262 |
| 2008/0034061 | A1 | | 2/2008 | Beares |
| 2008/0045236 | A1 | | 2/2008 | Nahon et al. |
| 2008/0085499 | A1 | * | 4/2008 | Horvath ........................ 434/262 |
| 2008/0293025 | A1 | * | 11/2008 | Zamierowsi et al. ......... 434/262 |

OTHER PUBLICATIONS

Greg Welch, et al. 3D Telepresence for Off-Line Surgical Training and On-Line Remote Consultation, May 11, 2005. http://www.cs.unc.edu/~welch/media/pdf/Welch2004_CREST.pdf. Last accessed Oct. 25, 2007. 44 pages.

Greg Welch, et al. Complementary Tracking and Two-Handed Interaction for Remote 3D Medical Consultation with a PDA. http://www.cs.unc.edu/Research/stc/publications/Welch_Track4VE2007_TwoHanded.pdf. Last accessed Oct. 25, 2007. 4 pages.

Michael Kanellos. Under-the-skin ID Chips Move Toward U.S. Hospitals. News.com, published on ZDNet News, Jul. 27, 2004. http://news.zdnet.com/2100-9584_22-5285815.html. Last accessed on Nov. 2, 2007. 12 pages.

* cited by examiner

SURGICAL PROCEDURE CAPTURE, MODELLING, AND EDITING INTERACTIVE PLAYBACK

BACKGROUND

Training surgeons has traditionally been a process of studying static book material, dissecting cadavers, observing surgical procedures, and finally performing the procedure under close supervision. While often a successful approach, considerable efforts have been directed to using technology to expand training options, beyond "see one, do one, and teach one." The need exists because frequently certain surgical procedures are infrequently needed though nonetheless important and surgeons who need to learn may not have an opportunity otherwise to experience this technique. In addition, certain surgical specialties are not available in the local area. Another complication is that the risks of a mistake by an inexperienced surgeon are very high, limiting circumstances under which a first procedure can be entrusted to a novice. In summary, the learning curve to successful surgery is steep and normally fraught with failure but is a normal part of learning. Some of the best acknowledged training is self-experienced procedure repetition.

To address these needs to a certain degree, considerable development has occurred in remote teleconferencing so that viewing or consulting can occur across geographic distances. These communication links can include interfacing to diagnostic imaging systems as well as audio and video of a surgical procedure. Typically, two-dimensional video editing techniques with no interaction are available to create training aids for later playback.

This remote viewing has been extended to remotely performed surgeries. Experimental remote surgery has been conducted as a means for expanding the range of medical services that can be provided to remotely stationed personnel, such as in extremely rural areas, oil rigs, ocean-going vessels, etc. The remote surgery can also be used for microsurgery or other instrumentalities that rely upon the precision of a surgery apparatus. To an extent, training can be simulated with such systems with recorded diagnostic or video imaging, taking advantage of their repeatable controls.

In addition, three-dimensional models of human anatomy have been constructed along with simulated surgical instruments that seek to create a virtual reality surgical training experience. Haptic feedback has been provided in some instances to simulate forces required to perform the procedure. Generally these models build upon Computer Aided Design (CAD) technology with static or crudely dynamic representations and false or non-photorealistic color rendering. Haptic feedback with simulated surgical instruments has also been incorporated into such training.

SUMMARY

The following presents a simplified summary of the innovation in order to provide a basic understanding of some aspects described herein. This summary is not an extensive overview of the claimed subject matter. It is intended to neither identify key or critical elements of the claimed subject matter nor delineate the scope of the subject innovation. Its sole purpose is to present some concepts of the claimed subject matter in a simplified form as a prelude to the more detailed description that is presented later.

The subject innovation relates to systems and/or methods that provide a degree of reality for virtual surgical training by capturing realistic imagery of actual surgical procedures with the interactive potential of modeling and animation tools. Thereby a novice can be monitored for successful and erroneous surgical inputs that pace playback of a four-dimensional model.

In accordance with one aspect of the subject innovation, a method is provided for generating surgical procedure training media. Three-dimensional data is captured over time of a portion of a patient's body undergoing a surgical procedure. Visual imagery of an exposed portion of the patient's body is captured. An orientation of a surgical instrument is detected relative to the patient's body during the surgical procedure. A four-dimensional image model (3D image plus time) of the portion of the patient's body during the procedure is created. Training media can be edited for playback of the four-dimensional model.

In another aspect, an apparatus is provided for generating surgical procedure training media. A 2D image and 3D capturing component records images and three-dimensional imaging data over time of a portion of a patient's body undergoing a surgical procedure. A spatial detection system detects an orientation of a surgical instrument relative to the patient's body during the surgical procedure. A modeling component creates a four-dimensional model (3D model plus time) of the portion of the patient's body. A user interface edits training media for playback of the four-dimensional model.

In yet a further aspect, an apparatus is provided for generating surgical procedure training media. A 3D capturing component records images and three-dimensional data over time of a portion of a patient's body undergoing a surgical procedure. A spatial detection system detects an orientation of a surgical instrument relative to the patient's body during the surgical procedure. A modeling component creates a four-dimensional model of the portion of the patient's body. A user interface processes the training media for interactive playback of the four-dimensional model. An interactive player responds to a spatially detected simulated surgical instrument to pace playback of the edited training media.

The following description and the annexed drawings set forth in detail certain illustrative aspects of the claimed subject matter. These aspects are indicative, however, of but a few of the various ways in which the principles of the innovation may be employed and the claimed subject matter is intended to include all such aspects and their equivalents. Other advantages and novel features of the claimed subject matter will become apparent from the following detailed description of the innovation when considered in conjunction with the drawings.

DETAILED DESCRIPTION

Figure 1:
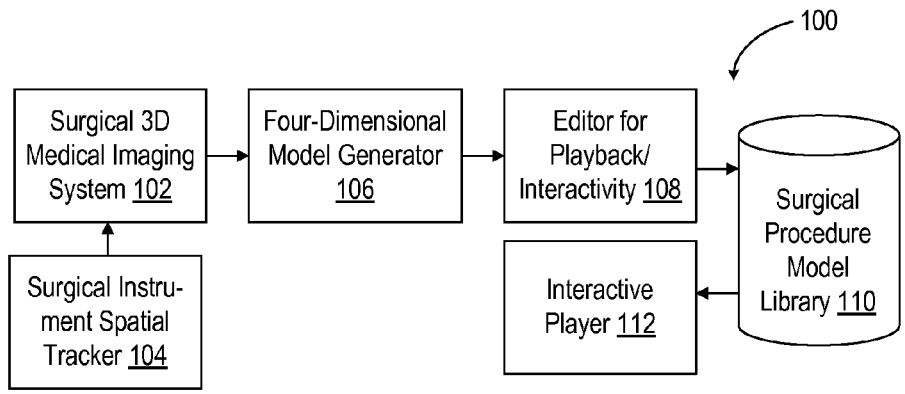
FIG. 1 illustrates a block diagram of an exemplary system that facilitates modeling and editing of a captured surgical procedure for training purposes.

A system for generating surgical procedure training media draws upon the realistic data of an actual surgical procedure for realistic training without the risks of a novice actually performing the procedure. A three-dimensional (3D) capturing component records images and three-dimensional data over time of a portion of a patient's body undergoing a surgical procedure. A six degrees of freedom (6 DOF) spatial detection system detects an orientation of a surgical instrument relative to the patient's body during the surgical procedure. A modeling component creates a four-dimensional model of the portion of the patient's body. Animation such as contingent events, trainee prompts, a virtual surgical instrument, etc., can be added to the model to expand upon the training potential. A user interface processes training media for interactive playback of the four-dimensional model plus haptics including defining triggers responsive to trainee simulated surgical inputs to pace sequencing of playback. An interactive player responds to a spatially detected simulated surgical instrument by pacing playback of the editing training media.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation.

As utilized herein, terms "component," "system," "interface," "store," "device," "network," "cloud," and the like are intended to refer to a computer-related entity, either hardware, software (e.g., in execution), and/or firmware. For example, a component can be a process running on a processor, a processor, an object, an executable, a program, a function, a library, a subroutine, and/or a computer or a combination of software and hardware. By way of illustration, both an application running on a server and the server can be a component. One or more components can reside within a process and a component can be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Specifically, the subject innovation can be utilized with a variety of hardware configurations such as, but not limited to disability assisted input/output facilities, voice enabled input/output, tactile (e.g., Braille, etc.) keyboard, etc. Of course, those skilled in the art will recognize many modifications may be made to this configuration without departing from the scope or spirit of the claimed subject matter. Moreover, the word "exemplary" is used herein to mean serving as an example, instance, or illustration. Any aspect or design described herein as "exemplary" is not necessarily to be construed as preferred or advantageous over other aspects or designs.

Now turning to the figures, FIG. 1 illustrates a system 100 that creates realistic, interactive training media of a surgical procedure. A three-dimensional medical imaging system 102 captures a portion of a patient's body. A surgical instrument spatial tracker 104 identifies the 6 DOF position of a surgical instrument relative to the patient's body. This information is used by a four-dimensional model generator 106 to create a model of the procedure.

Medical imaging refers to the techniques and processes used to create images of the human body (or parts thereof) for clinical purposes (medical procedures seeking to reveal, diagnose or examine disease) or medical science (including the study of normal anatomy and function). As a discipline and in its widest sense, it is part of biological imaging and incorporates radiology (in the wider sense), radiological sciences, endoscopy, (medical) thermography, medical photography and microscopy (e.g. for microsurgery-level resolution). Measurement and recording techniques which are not primarily designed to produce images, such as electroencephalography (EEG) and magnetoencephalography (MEG) and others, but which produce data susceptible to be represented as maps (i.e. containing positional information), can be seen as forms of medical imaging.

In another aspect, a 3D camera is capable of recording a three-dimensional image of a scene through a single lense. In another aspect, a plurality of 2D videocameras can be combined through stereo photogrammetry.

To capture the visual environment of the original procedure, in one aspect multiple 2D or 3D cameras can cover multiple angles so that the surgeon and the surgical instruments do not wholly obstruct certain portions. Alternatively or in addition, views of these hidden portions are modeled when viewable and then skinned onto a model of that surface whose position is analytically extrapolated from those portions that are viewed.

The six degrees of freedom of each surgical instrument is advantageously captured, as well as sufficient force transducers to detect haptic sensations. Supplemental tissue force measurements can be captured to extend a haptic model to a wider area of interaction or with a wider array of instruments or a wider variety of tissue manipulations. For example, a surgeon might palpate the target tissue plus areas around the target with his scalpel to document the feeling of the tissue-scalpel interaction before each cut. Also, a range of scalpel motions can be explored, to include slicing, poking, piercing, etc., at varying speeds to capture during tissue responses and haptic sensations.

A user interface editor 108 enhances the four-dimensional model for playback/trainee interaction, such as defining input events that will allow normal playback to proceed or that can trigger a contingent animation for an erroneous input. Alternatively or in addition, model elements can be "skinned", that is texture mapped, for a realistic color and texture for such types of tissues. The edited training media is then stored in a surgical procedure model library 110 for later playback by an interactive player 112.

Advantageously, in some aspects, all indications of the surgeon and the original surgical instruments are removed from the model and playback from the perspective of the student. Alternatively or in addition, the original procedure can be replayed, perhaps with varied playback speeds and orientations, with the surgeon's hands and instrument(s) in view so that the student can witness a correctly performed procedure. Alternatively or in addition, the student can be cued toward the correct motion with visual cues derived from the original instrument positions, either prospectively or retroactively.

In another aspect, actual tissue interaction in the haptic domain can be captured during the procedure in addition to the above 4D visual data. The capturing of the haptic data could be accomplished with a six degree of freedom force transducer mounted on the surgical instrument, recording the forces the surgeon feels. This haptic data would be processed along with the visual data 4D data to create a complete visual and haptic data base that could then be explored with a simulated instrument, beyond and within reason the spatial and time path experienced but the surgeon.

Certain haptic sensations captured during the procedure would have to be processed with the visual data to produce the required many-dimensional model of haptic feedback for training interaction, especially if the student departs from the exact movements of the surgeon. When, for example, a surgeon cuts through tissue, there is the initial compliant forces felt when in first contact with knife and tissue. At this initial contact, before the knife penetrates the tissue, static friction adheres the point of the knife to the contacted place on the tissue, imparting a number of dimensions of haptic feedback forces felt: Z displacement compliance and viscosity as the scalpel is pushed into the tissue; X and Y displacement compliance as the scalpel is moved horizontally and vertically across the tissue; and a Rotation compliance and viscosity as the scalpel is attempted to roll along its axis. This can be equated to using a knife to interact with a balloon filled with Jello. Before penetration, you would feel a spring-like compliance as well as a viscous feel in X, Y, Z and Roll. If enough force were applied to the knife in the Z direction, the outside layer would be penetrated and the forces would instantly change to those of interacting with Jello. Thus for example, when the student is exploring the tissue with the simulated instrument, the player would need to know whether to playback haptic data before penetration or after, two possibly differing haptic experiences. The haptic experience may in fact be an empirical model derived from the recorded data. It is important to process the haptic and visual data together in order to derive a model for tissue interaction. The interactive playback needs to show the tissue in its undistorted shape, before the surgeon interacts with it as well as when interacted with an instrument so a reasonable physical response to these instrument forces needs to be simulated With the above 3D visual data plus time and this additional haptic data, the interactive player would allow the student to interact with the patient's tissue using simulated surgical instruments with a reasonable expectation of good haptic and visual fidelity, even if the surgeon's original movements weren't exactly followed.

Figure 2:
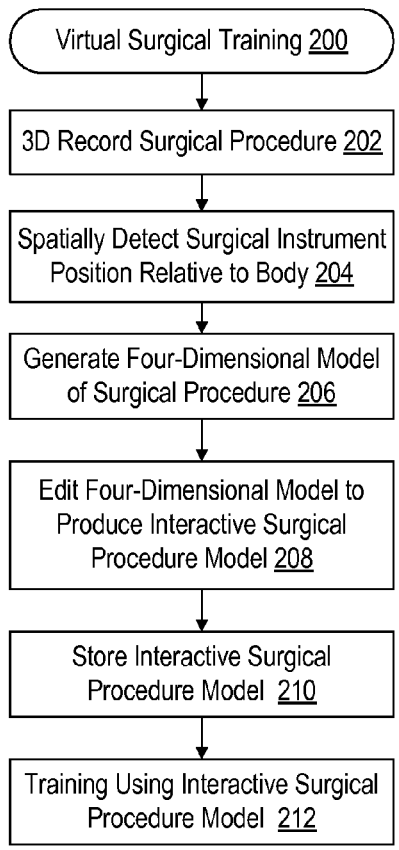
FIG. 2 illustrates a methodology performed by the system of FIG. 1.

FIG. 2 illustrates methodologies and/or flow diagrams in accordance with the claimed subject matter. For simplicity of explanation, the methodologies are depicted and described as a series of acts. It is to be understood and appreciated that the subject innovation is not limited by the acts illustrated and/or by the order of acts. For example acts can occur in various orders and/or concurrently, and with other acts not presented and described herein. Furthermore, not all illustrated acts may be required to implement the methodologies in accordance with the claimed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device, carrier, or media.

A virtual surgical training methodology 200 begins in block 202 by recording three-dimensional medical imaging of a surgical procedure. In block 204, a surgical instrument utilized in the surgical procedure is spatially detected relative to the medically imaged portion of the patient's body. A four-dimensional model of the surgical procedure is generated in block 206. The created four-dimensional model is edited to enhance interactivity for training in block 208. For example, the pacing of playback can be made contingent upon placement of a simulated surgical instrument into a motion corresponding to the actual surgical instrument. Animations can be incorporated that are triggered to playback in response to erroneous placement events, such as intersecting (i.e., virtually piercing or cutting) tissue in the wrong location, use of wrong surgical instrument, etc. Prompts can be added to instruct a trainee for expected inputs for interactive playback. Realistic coloration/texture/lighting can be added, especially for a model based upon a nonvisual medical imaging modality. The edited training media is then stored in a surgical procedure model library 110 for accessing from an interactive player 112. Such playback can advantageously include three-dimensional rendering with binocular visors, selective eye filters (e.g., blue/red, orthogonally polarized, rapidly selectively transparent right and left lenses). The interactive player can receive inputs from a user simulating a surgical input in order to interact with the model.

Figure 3:
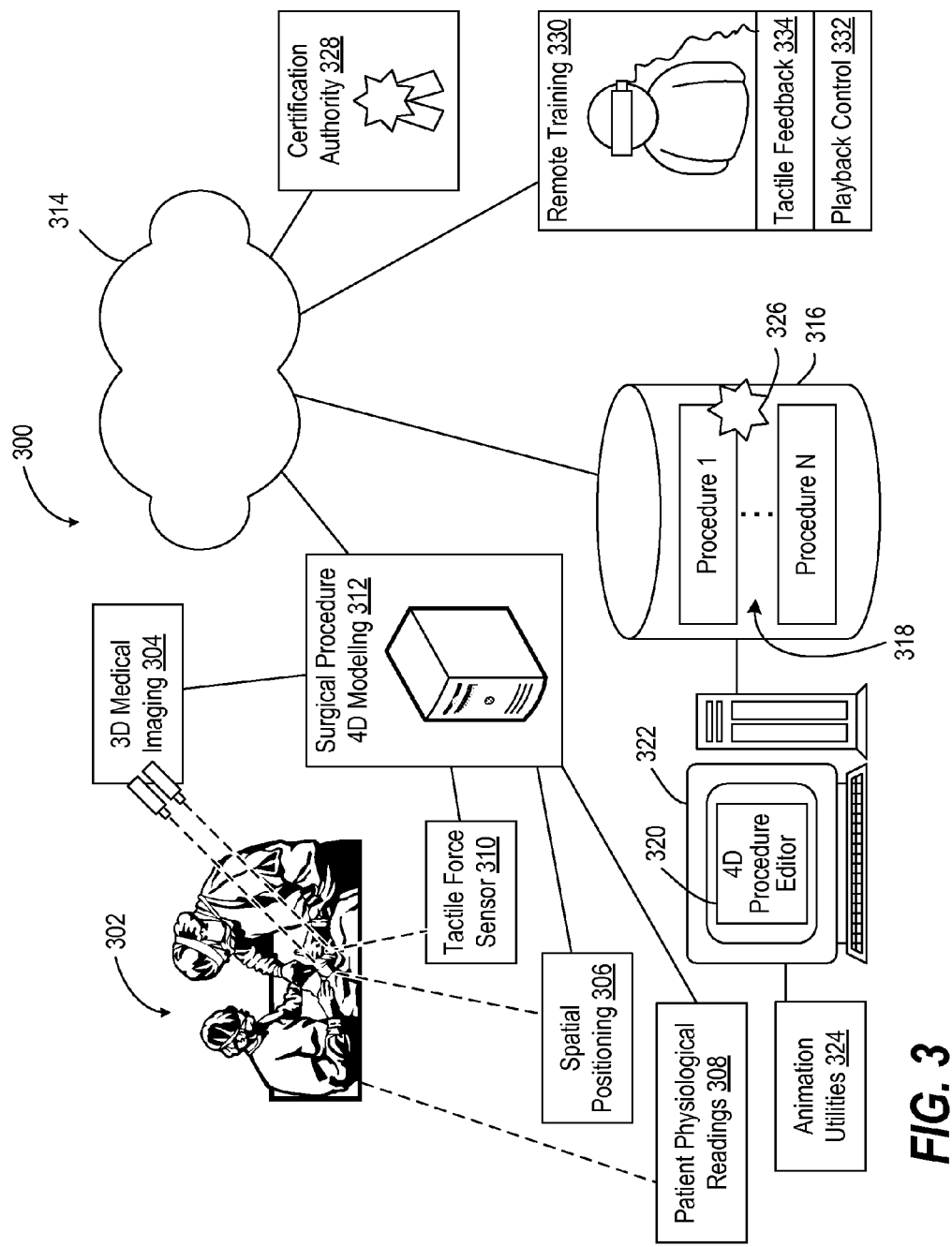
FIG. 3 illustrates a block diagram of another exemplary system that facilitates capture, modeling, and editing of a virtual surgery for training purposes.

In FIG. 3, a virtual surgical training system 300 captures a surgical procedure, depicted at 302. Although an open surgical procedure is illustrated, it should be appreciated that the procedure may include in whole or in part endoscopic or laparoscopic techniques, vascular catheterization, microsurgical techniques, or noninvasive directed energy techniques. Three-dimensional medical imaging 304 produces data sufficient for creating a three-dimensional model, such as vector representation in a Computer Aided Design (CAD) system. The medical imaging captured over time creates a four-dimensional capture of the surgical procedure. For medical imaging that is not visual, the model can be augmented by visual recordings of the appearance of certain types of tissue as seen by a surgeon during the procedure for associating with portions of the nonvisual imagery. For modalities of medical imaging lacking three-dimensional spatial references, a spatial positioning system 306 can be incorporated to detect changes in position of portions of the patient's body, positions of surgical instruments relative to the patient's body, etc. Certain outputs from operating room monitors, depicted as patient physiological readings 308, can also be recorded, time tagged with the imagery, to provide additional realism. In certain applications, active tactile feedback to a trainee can be facilitated by recording the tactile force experienced at the actual surgical instruments by tactile force sensors 310 (e.g., piezoelectric transducer, strain gauge, etc.). These inputs are collected and processed by a surgical procedure 4D modeling system 312.

Although the various aspect of the system 300 can be locally provided, in the illustrative depiction a distributed network (e.g., ad hoc network, private Wide Area Network (WAN), Internet, etc.) 314 can link various components. For example, a storage component 316 is provided for storing edited models received from the modeling component 312 or training media depicted as procedures 1 . . . N 318, the latter having been edited by a 4D procedure editor 320 executed on a workstation 322. The editor 320 can draw upon resources from animation utilities 324, such as skinning the model with realistic colors/textures (including internal portions exposable by scalpel), defining a lighting scheme, defining a virtual surgical instrument to controlled by a trainee, etc. A digital certification 326 can be given to a procedure 318, such as from a trusted certification authority 328.

Training is then accomplished by a remote training system 330, which can entail in whole or in part a general purpose work station with interactive inputs made via various pointing devices. Advantageously, a simulated surgical instrument can incorporate positional feedback, force/strain feedback, acceleration sensing, etc., depicted as playback control 332. Mechanical resistance (tactile) feedback 334 can be incorporated to enhance realism, such as varying the amount of force required to pierce through different types of tissues by a scalpel.

Figure 4:
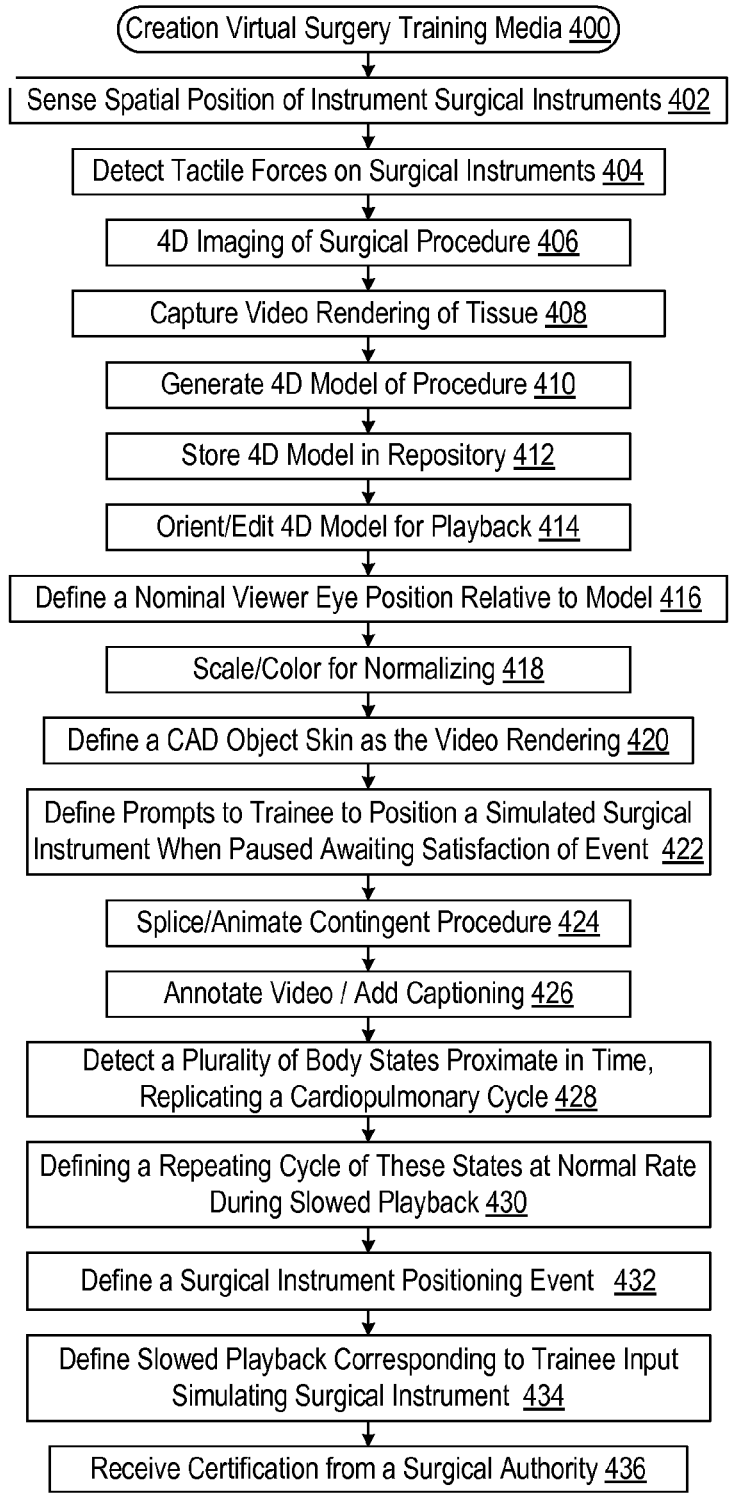
FIG. 4 illustrates a flow diagram of a methodology performed by the system for creating and editing training media of FIG. 3.

In FIG. 4, a methodology 400 for creating training media is depicted. In block 402, spatial position of surgical instruments are sensed. For example, in an ultrasonic or magnetic resonance imaging guided procedures, the surgical instrument can be detected with the imaging system and removed with digital processing for 3D model created with stereoscopic video cameras. The texture map if the remaining viewable tissue can be processed to remove shadows from the surgeon's instrument that could influence the captured texture appearance of the resulting 3D model. In another aspect, diagnostic 3D data that is combined with 2D video imagery can use other techniques to delete the instrument from the model. Triangulation of visual imagery or other electromagnetic signal from the surgical instrument can be detected by sensors. In block 404, tactile forces imparted by the surgical instrument are detected. For example, a pressure sensitive layer on an end effector or on a handle could be monitored. As another example, a strain gauge between components of an instrument could be monitored. In block 406, a surgical procedure is 3D captured over time to achieve a four-dimensional (4D) image. In block 408, video rendering of tissue is captured, which may augment a nonvisual medical imaging system or be a separate library with rendering definitions for various types of tissues, including subtypes for the same type of tissue (e.g., diseased). In block 410, the data is processed to generate a 4D model of a portion of the patient's body. In an illustrative embodiment, positioning and displacement of tissue is included in the model with events associated with external actuators and instruments correlated but removed from the actual model. In block 412, the unedited 4D model is stored in a repository.

In block 414, the 4D model is retrieved for editing and oriented to a convenient size and position. Editing can include removal of artifacts and extraneous devices. Portions of the procedure can be deleted to shorten playback, adjusting the model to make any discontinuities less apparent. In block 416, a nominal viewer eye position relative to the model can be defined. In block 418, the 4D model can be scaled or colored, such as for normalizing, which can have benefits in splicing together multiple 4D models. In block 420, for medical imaging that lacks visual information, separately ascertained visual characteristics can be applied to "skin" portions of the model, including attributes for cutaway. Even with visual imagery obtained in the first instance, it may be desirable to recolor the model for privacy of the patient, to remove uncharacteristic conditions, etc. In block 422, prompts to the trainee can be defined to position a simulated surgical instrument. Such prompts can occur at points in the playback wherein the 4D model is paused, awaiting satisfaction of a surgical instrument event.

In block 424, the model can be spliced together with animated portions or other surgical procedures that proceeded differently from a given point. For example, a decision branch in the procedures, either as an accepted alternative or as a mistaken error, can be inserted to increase a range of possible training interaction. For example, sensed simulated placement of a surgical instrument into an artery can trigger an animation of excessive bleeding with physiological readings changed to correspond to a decrease in blood pressure and pulse. As another example, different accepted surgical techniques can be spliced into the training media for selection, such as by normalizing 4D models from different surgical procedures on different patients to similar dimensions. In block 426, the training media can be visually or audibly annotated, such as replacing or adding narration, callouts of anatomical points of interest, mentions of steps taken that are not apparent (e.g., electrical settings of an ablation device), etc. Captioning can be added, such as for further information, alternative languages, etc.

In one illustrative version, in block 428 a plurality of body states can be marked or automatically detected (e.g., by maximum and minimum positions, electrocardiogram signal, etc.). In order to enhance the realism, the 4D model can be made to repeat a movement cycle corresponding to respiration, heartbeat, pulse, etc., in block 430. By so doing, even when playback is slowed or speeded up to an optimum training playback rate, the viewed portion of the body can appear to be at normal time rate.

In block 432, a surgical instrument positioning event is defined, which can correspond to a tracked event in the actual imaged surgery. For example, the 4D model can then be paused in block 434, repeating the simulated cardiopulmonary activity, until the tissue is affected by a simulated surgical instrument. In block 436, certification is received from a surgical authority to validate/verify the edited training media.

Figure 5:
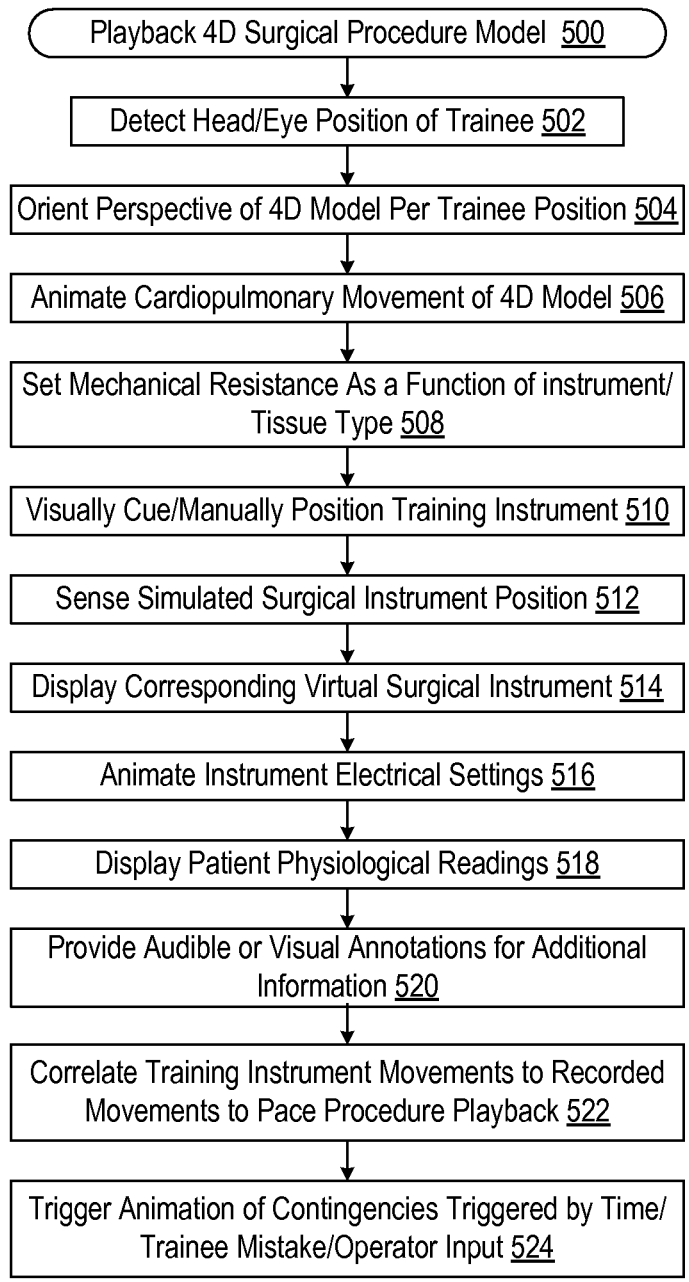
FIG. 5 illustrates a flow diagram of a methodology for playback of training media performed by the system of FIG. 3.

In FIG. 5, a methodology 500 is depicted for interactive playback of the 4D surgical model. In block 502, a head/eye position of a trainee are detected in order to enhance the realism by orienting the perspective of the 4D model per the trainee position in block 504. In block 506, a cardiopulmonary movement cycle is imparted to the 4D model. In block 508, mechanical response is set as a function of instrument type and type of tissue virtually encountered as positioned. Visual cues can be provided for manually positioning a training instrument to simulate a surgical instrument in block 510. A position of a pointing device is sensed as a simulated surgical instrument in block 512. In block 514, a corresponding virtual instrument is displayed relative to the 4D model with movement corresponding to the trainee input. For procedure requiring surgical instrument settings, such as for ablation devices, interactive animated controls can be displayed in block 516. To further inform the training, physiological readings can be simulated or played back in block 518. Audible or visual annotations can be displayed for additional information in block 520. Movement of the training instrument (pointing device) can be used to pace procedure playback in block 522, such as pausing a displayed change to the tissue to correspond to the virtual interaction with the instrument. In block 524, proceeding playback can be made to activate a contingency by an external input, such as from an instructor inserting a complication, by an erroneous use of the surgical instrument (e.g., bleeding), or by a time-triggered event (e.g., irregular cardiac rhythm).

It should be appreciated that three-dimensional display can be unavailable or undesirable in certain instances, such as when others view the procedure or when the procedure is normally accomplished viewing a remote 2D display such as in endoscopy. As such, the display can be augmented by, or solely comprise, a two-dimensional rendering of the three-dimensional model.

Figure 6:
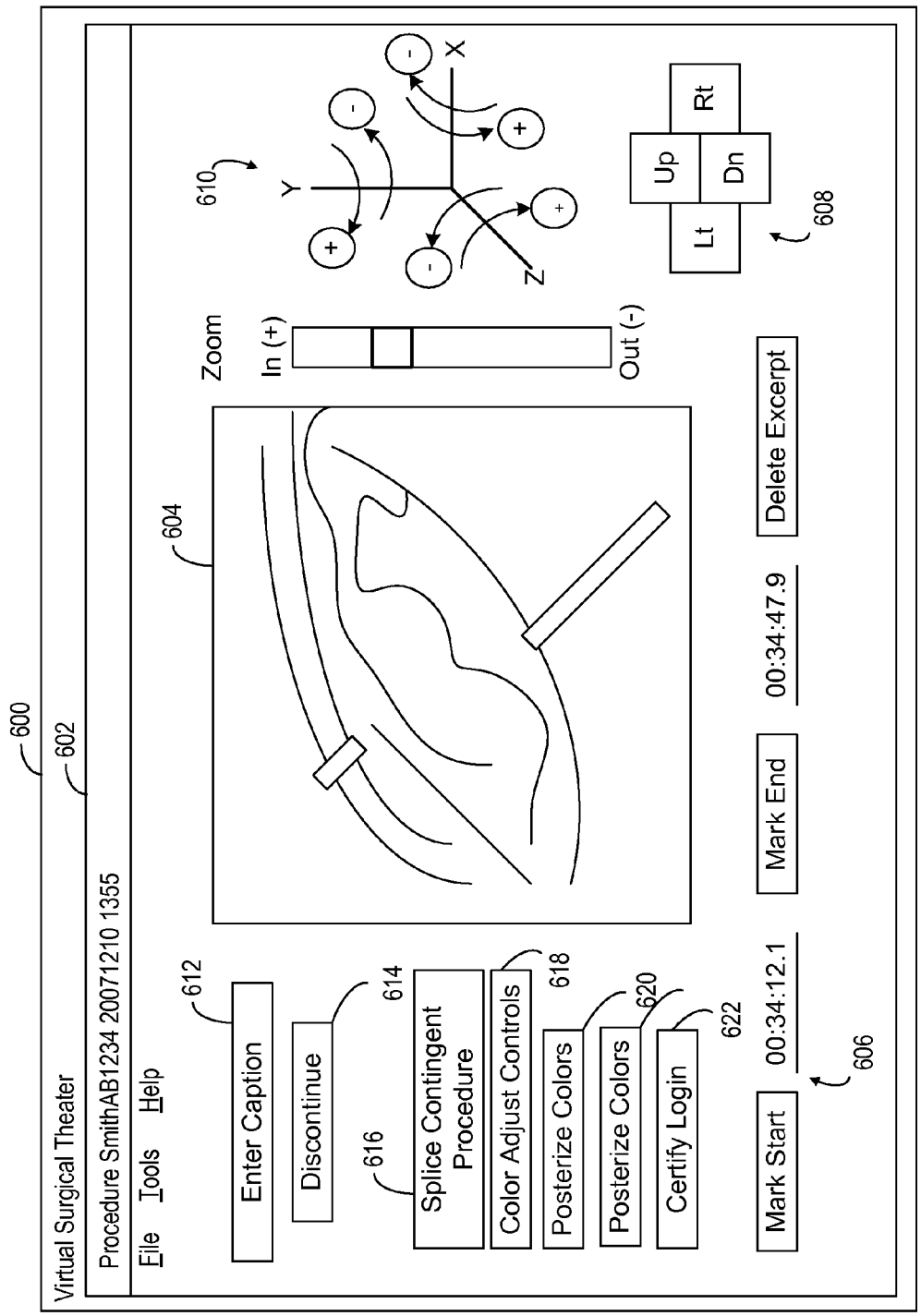
FIG. 6 illustrates a diagram of an editing graphical user interface for the system of FIG. 3.

In FIG. 6, a graphical user interface ("virtual surgical theater") 600 is depicted for editing a four-dimensional model of a surgical procedure ("Procedure SmithAB1234 20071210 1355") 602. A window 604 shows a current view of the model as edited. Portions can be deleted with controls depicted at 606. Scaling and positioning controls 608 and orientation controls 610 can set a nominal trainee viewing position. Annotations, such as an entered caption input 612 that can later be discontinued by a control 614, can provide additional information or prompts. A separate splice contingent procedure window control 616 can expand upon the interaction possibilities. Color adjust controls 618 can be activated to render the view less realistic for nonmedical trainees or more realistic for trainees that would so benefit. A posterize colors control 620 is an example of predefined image processing algorithm to normalize or simplify the depiction. A certify login control 622 gains access to additional features for digitally certifying an edited training media file.

Figure 7:
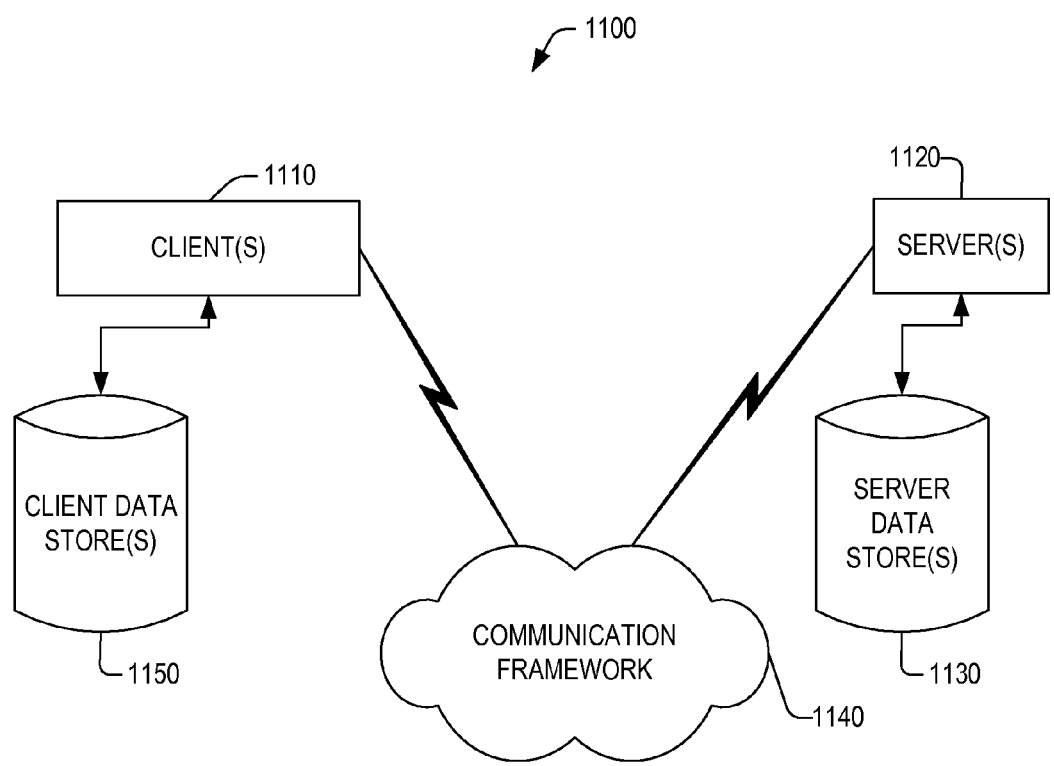
FIG. 7 illustrates an exemplary networking environment, wherein the novel aspects of the claimed subject matter can be employed.
Figure 8:
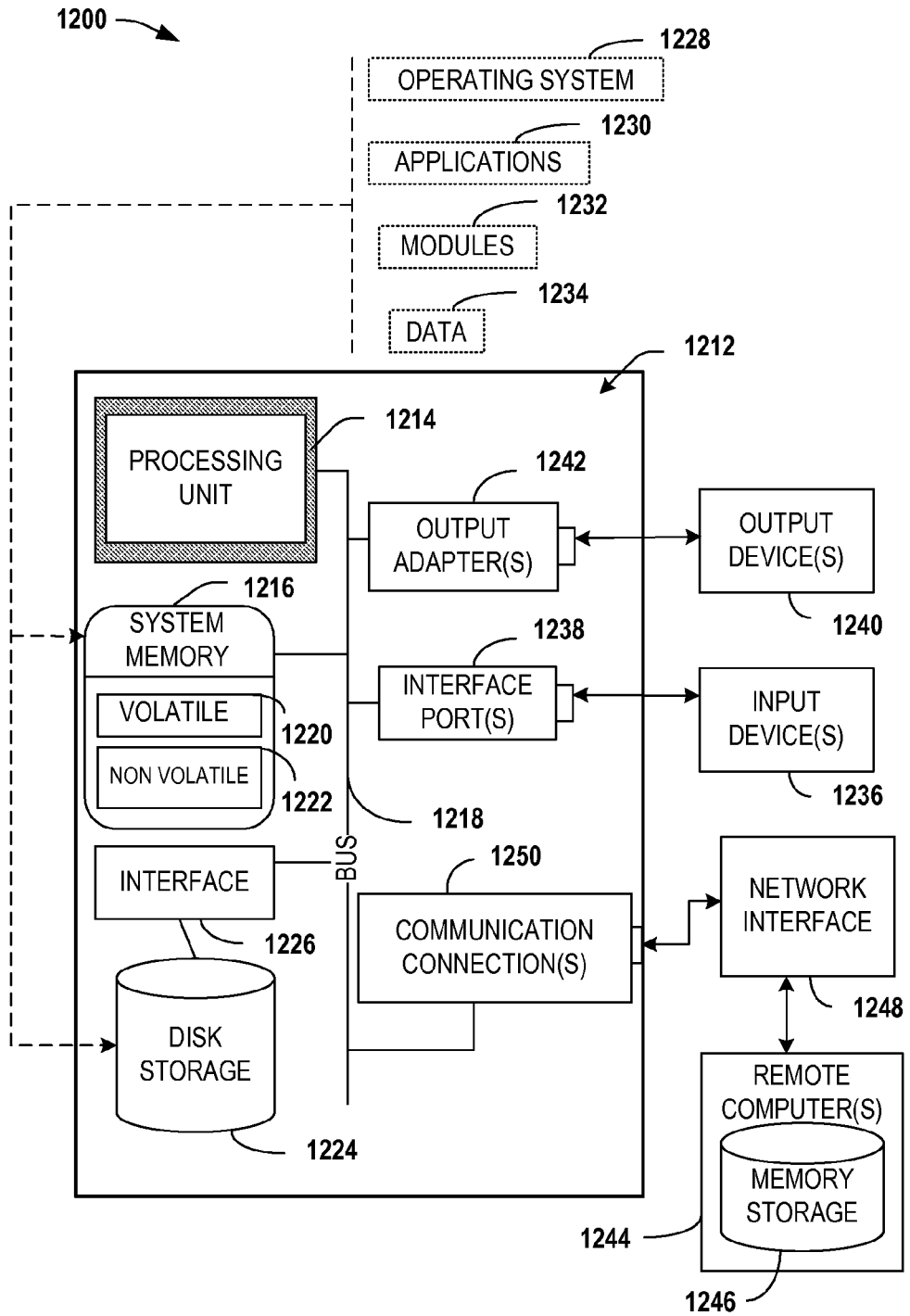
FIG. 8 illustrates an exemplary operating environment that can be employed in accordance with the claimed subject matter.

In order to provide additional context for implementing various aspects of the claimed subject matter, FIGS. 7-8 and the following discussion is intended to provide a brief, general description of a suitable computing environment in which the various aspects of the subject innovation may be implemented. For example, a counselor component that facilitates automatically generating questions to ask a doctor during an appointment, as described in the previous figures, can be implemented in such suitable computing environment. While the claimed subject matter has been described above in the general context of computer-executable instructions of a computer program that runs on a local computer and/or remote computer, those skilled in the art will recognize that the subject innovation also may be implemented in combination with other program modules. Generally, program modules include routines, programs, components, data structures, etc., that perform particular tasks and/or implement particular abstract data types.

Moreover, those skilled in the art will appreciate that the inventive methods may be practiced with other computer system configurations, including single-processor or multiprocessor computer systems, minicomputers, mainframe computers, as well as personal computers, hand-held computing devices, microprocessor-based and/or programmable consumer electronics, and the like, each of which may operatively communicate with one or more associated devices. The illustrated aspects of the claimed subject matter may also be practiced in distributed computing environments where certain tasks are performed by remote processing devices that are linked through a communications network. However, some, if not all, aspects of the subject innovation may be practiced on stand-alone computers. In a distributed computing environment, program modules may be located in local and/or remote memory storage devices.

FIG. 7 is a schematic block diagram of a sample-computing environment 1100 with which the claimed subject matter can interact. The system 1100 includes one or more client(s) 1110. The client(s) 1110 can be hardware and/or software (e.g., threads, processes, computing devices). The system 1100 also includes one or more server(s) 1120. The server(s) 1120 can be hardware and/or software (e.g., threads, processes, computing devices). The servers 1120 can house threads to perform transformations by employing the subject innovation, for example.

One possible communication between a client 1110 and a server 1120 can be in the form of a data packet adapted to be transmitted between two or more computer processes. The system 1100 includes a communication framework 1140 that can be employed to facilitate communications between the client(s) 1110 and the server(s) 1120. The client(s) 1110 are operably connected to one or more client data store(s) 1150 that can be employed to store information local to the client(s) 1110. Similarly, the server(s) 1120 are operably connected to one or more server data store(s) 1130 that can be employed to store information local to the servers 1120.

With reference to FIG. 8, an exemplary environment 1200 for implementing various aspects of the claimed subject matter includes a computer 1212. The computer 1212 includes a processing unit 1214, a system memory 1216, and a system bus 1218. The system bus 1218 couples system components including, but not limited to, the system memory 1216 to the processing unit 1214. The processing unit 1214 can be any of various available processors. Dual microprocessors and other multiprocessor architectures also can be employed as the processing unit 1214.

The system bus 1218 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1216 includes volatile memory 1220 and nonvolatile memory 1222. The basic input/output system (BIOS), containing the basic routines to transfer information between elements within the computer 1212, such as during start-up, is stored in nonvolatile memory 1222. By way of illustration, and not limitation, nonvolatile memory 1222 can include read only memory (ROM), programmable ROM (PROM), electrically programmable ROM (EPROM), electrically erasable programmable ROM (EEPROM), or flash memory. Volatile memory 1220 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 1212 also includes removable/non-removable, volatile/non-volatile computer storage media. FIG. 8 illustrates, for example, a disk storage 1224. Disk storage 1224 includes, but is not limited to, devices like a magnetic disk drive, floppy disk drive, tape drive, Jaz drive, Zip drive, LS-100 drive, flash memory card, or memory stick. In addition, disk storage 1224 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1224 to the system bus 1218, a removable or non-removable interface is typically used such as interface 1226.

It is to be appreciated that FIG. 8 describes software that acts as an intermediary between users and the basic computer resources described in the suitable operating environment 1200. Such software includes an operating system 1228. Operating system 1228, which can be stored on disk storage 1224, acts to control and allocate resources of the computer system 1212. System applications 1230 take advantage of the management of resources by operating system 1228 through program modules 1232 and program data 1234 stored either in system memory 1216 or on disk storage 1224. It is to be appreciated that the claimed subject matter can be implemented with various operating systems or combinations of operating systems.

A user enters commands or information into the computer 1212 through input device(s) 1236. Input devices 1236 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1214 through the system bus 1218 via interface port(s) 1238. Interface port(s) 1238 include, for example, a serial port, a parallel port, a game port, and a universal serial bus (USB). Output device(s) 1240 use some of the same type of ports as input device(s) 1236. Thus, for example, a USB port may be used to provide input to computer 1212 and to output information from computer 1212 to an output device 1240. Output adapter 1242 is provided to illustrate that there are some output devices 1240 like monitors, speakers, and printers, among other output devices 1240, which require special adapters. The output adapters 1242 include, by way of illustration and not limitation, video and sound cards that provide a means of connection between the output device 1240 and the system bus 1218. It should be noted that other devices and/or systems of devices provide both input and output capabilities such as remote computer(s) 1244.

Computer 1212 can operate in a networked environment using logical connections to one or more remote computers, such as remote computer(s) 1244. The remote computer(s) 1244 can be a personal computer, a server, a router, a network PC, a workstation, a microprocessor based appliance, a peer device or other common network node and the like, and typically includes many or all of the elements described relative to computer 1212. For purposes of brevity, only a memory storage device 1246 is illustrated with remote computer(s) 1244. Remote computer(s) 1244 is logically connected to computer 1212 through a network interface 1248 and then physically connected via communication connection 1250. Network interface 1248 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereof, packet switching networks, and Digital Subscriber Lines (DSL).

Communication connection(s) 1250 refers to the hardware/software employed to connect the network interface 1248 to the bus 1218. While communication connection 1250 is shown for illustrative clarity inside computer 1212, it can also be external to computer 1212. The hardware/software necessary for connection to the network interface 1248 includes, for exemplary purposes only, internal and external technologies such as, modems including regular telephone grade modems, cable modems and DSL modems, ISDN adapters, and Ethernet cards.

It should be appreciated with the benefit of the foregoing that applications consistent with aspects herein can provide a relatively high-fidelity, interactive viewing and tactile (haptic) environment for practicing a surgical procedure. By interactivity, reference is made to enabling a student to manipulate simulated surgical instrument(s) that interact with tissue in a believable visual and tactile environment. Advantageously, the student need not reproduce the exact motions made during the creation of the environment. Therefore, it should be appreciated that the playback of the model is not necessarily an exact recreation of the exact surgical procedure recorded to create the model, displayed with or without the surgeon and instruments. In some instances, the student is allowed to manipulate the 3D model in a three-dimensional path within an acceptable deviation from the surgeon's path. It should be appreciated that the deviation can be acceptable within the constraints of the model for instruction purposes yet lie outside of the realm of an acceptable path as defined by the standard of care or the surgical technique.

Alternatively or in addition, capturing a full 3D environment over time (4D) enables a playback device to interactively play back the visual 3D environment (i.e., a 3D model of the tissue and original instrument with specific tissue interactions) with respect to time. Interactivity can be limited during student playback to exactly to same motions as the recorded surgeon, but with changes in a time sequence (e.g., slow motion, fast forward, pause, normal playback, etc.) or vantage point perspective (e.g., zoom in, zoom out, skew orientation, etc.) that changes the camera point of view. This mode can ensure that the student sees an optimal or representative surgical procedure.

Alternatively or in addition, the student's interaction with the tissue can be rendered visually and tactically with a visual indication to cue the student either prospectively or retroactively with where the optimum tissue operations would have been performed.

For those areas of tissue that do not correspond exactly to the path chosen by the surgeon, the model can include characterizations and extrapolations of types of tissue to provide an amount of tactile resistance and response as well as believable visual deformations to a given surgical instrument that could be reasonably encountered. In addition, a range of surgical instruments can be instruments, to include scalpels, probes, resectors, tweezers, scissors, etc. Such haptic modeling can be multi-valued. Such modeling of haptic feedback can include resistance, elasticity, viscosity, compliance, etc., before and after being severed or repositioned. These forces can be correlated with three-dimensional determinations as well as anatomical recognition software. Modeling of the tissue deformation might include viscous reactions, liquid expulsion (bleeding) and other acts not directly predictable from only instrument contact.

Modeled playback of haptic feedback can correlate an orientation of the instrument with respect to a tissue surface, changing the force dynamically to correspond with speed and angle, for example distinguishing a slow pushing motion from a slicing motion from a piercing motion. These additional forces could be determined from a generic model for a scalpel for instance that has variables for blade size and sharpness, etc., with mathematically calculated or empirically determined forces that vary as a function of angle and tissue type. Nonhomogeneous measurements in haptic feedback can be duplicated with a sufficiently robust physical model. For example, a yield force can be determined that prompts a visual and haptic change in playback as the tissue yields to the instrument for a given six-degrees of freedom (6 DOF) orientation and orientation history with respect to the tissue.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

There are multiple ways of implementing the present innovation, e.g., an appropriate API, tool kit, driver code, operating system, control, standalone or downloadable software object, etc. which enables applications and services to use the advertising techniques of the invention. The claimed subject matter contemplates the use from the standpoint of an API (or other software object), as well as from a software or hardware object that operates according to the advertising techniques in accordance with the invention. Thus, various implementations of the innovation described herein may have aspects that are wholly in hardware, partly in hardware and partly in software, as well as in software.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A method for generating training media, comprising:
    capturing three-dimensional data over time of a portion of a human patient's body undergoing a surgical procedure, the capturing being performed at least in part by stereoscopic video cameras or by a three-dimensional camera;
    recording physiological readings over time of the portion of the human patient's body, the physiological readings comprise at least a movement cycle;
    capturing visual imagery of an exposed portion of the human patient's body;
    creating, using one or more processors, a four-dimensional model of the portion of the human patient's body based on the three-dimensional data, the physiological readings, and the visual imagery of the exposed portion of the human patient's body changing over time; and
    modifying at least a portion of the three-dimensional data or visual imagery of the human patient's body to maintain privacy of the human patient's body.

2. The method of claim 1, further comprising editing the training media for playback of the four-dimensional model by defining an object texture map for a viewed surface of the four-dimensional model to correspond to the captured visual imagery.

3. The method of claim 1, further comprising editing the training media by deleting a period of time from the four-dimensional model.

4. The method of claim 1, further comprising capturing an orientation of a surgical instrument relative to the human patient's body during the surgical procedure.

5. The method of claim 4, further comprising removing the surgical instrument from a spatial position the surgical instrument occupies in the four-dimensional model.

6. The method of claim 4, further comprising editing the training media by defining a surgical instrument placement event that causes playback to pause.

7. The method of claim 6, further comprising detecting a position of a simulated surgical instrument positioned by a trainee during playback of the training media.

8. The method of claim 7, further comprising rendering a virtual surgical instrument positioned in the training media corresponding to the simulated surgical instrument.

9. The method of claim 7, further comprising determining satisfaction of the simulated surgical instrument placement event to continue playback.

10. The method of claim 7, further comprising:
    defining an erroneous instrument placement event in the four-dimensional model; and
    in response to the erroneous instrument placement event, displaying a contingent training animation.

11. The method of claim 1, further comprising editing the training media by changing an orientation of the four-dimensional model to virtually position a trainee.

12. The method of claim 11, further comprising detecting a head and eye position of the trainee during playback and orienting the four-dimensional model based on the detected head and eye position of the trainee.

13. The method of claim 11, further comprising displaying a video differentiated for each eye of the trainee for a three-dimensional depiction.

14. The method of claim 1, further comprising:
selecting a second movement cycle that affects movement of the portion of the patient's body; and
playing back the four-dimensional model of the portion of the patient's body at an increased or reduced speed while rendering a sequence of movements caused by the movement cycle at a normal time rate, wherein the normal time rate is different than the increased or reduced speed, such that the sequence of movements are out of sync with the increased or reduced speed.

15. The method of claim 1, further comprising:
detecting haptic forces on a surgical instrument used in the surgical procedure;
correlating an orientation of the surgical instrument to a position in the four-dimensional model; and
creating a haptic feedback model for interaction by a simulated surgical instrument with the four-dimensional model.

16. An apparatus for generating surgical procedure training media, comprising:
one or more processors;
an image capturing component for recording three-dimensional imaging data over time of a portion of a human patient's body undergoing a surgical procedure;
a spatial detection system for capturing an orientation of a surgical instrument relative to the human patient's body during the surgical procedure;
a modeling component for creating, using the one or more processors, a four-dimensional model of the portion of the human patient's body based at least on the three-dimensional imaging data and the captured orientation of the surgical instrument and for defining a decision branch in the four-dimensional model and for modifying at least a portion of the three-dimensional imaging data of the human patient's body to maintain privacy of the human patient's body; and
a storage component for storing the four-dimensional model and at least one alternative four-dimensional model, wherein the alternative four-dimensional model is created from recorded three-dimensional data and captured orientations of a surgical instrument during a different surgical procedure performed on a different patient.

17. The apparatus of claim 16, further comprising a haptic data capturing component for capturing haptic data from the surgical instrument used in the surgical procedure.

18. The apparatus of claim 16, further comprising a triggering component for switching to a different decision branch of the four-dimensional model based at least in part upon a sensed simulated user action, the different branch corresponding to the four-dimensional model or the alternative four-dimensional model.

19. One or more computer storage media having instructions encoded thereupon that, when executed by one or more processors, cause a computing device to perform acts comprising:
capturing three-dimensional data over time of a portion of a human patient's body undergoing an actual open surgical procedure, the three-dimensional data being captured from at least a stereoscopic video camera or a three-dimensional camera;
capturing visual imagery of an exposed portion of the human patient's body;
capturing an orientation of a surgical instrument relative to the human patient's body during the actual surgical procedure;
capturing haptic forces on the surgical instrument during the actual surgical procedure;
creating a four-dimensional model of the portion of the human patient's body based on the three-dimensional data, the visual imagery of the exposed portion of the human patient's body, the orientation of the surgical instrument, and the haptic forces on the surgical instrument changing over time; and
recoloring at least a portion of the three-dimensional data or visual imagery of the human patient's body to maintain privacy of the human patient's body.

20. The computer storage media of claim 19, further comprising:
correlating an orientation of the surgical instrument to a position in the four-dimensional model;
creating a haptic feedback model based at least in part on the captured haptic forces for interaction by a simulated surgical instrument with the four-dimensional model;
editing training media by defining a surgical instrument placement event for the simulated surgical instrument that causes playback to pause; and
detecting a position of the simulated surgical instrument positioned by a trainee during playback of the training media.

21. The computer storage media of claim 20, further comprising:
defining an erroneous placement of the simulated surgical instrument in the four-dimensional model;
in response to the erroneous instrument placement event, displaying a contingent training animation;
further editing the training media by changing an orientation of the four-dimensional model to virtually position the trainee; and
orienting the four-dimensional model based at least in part on a detected head position of the trainee.

* * * * *